(12) United States Patent
Kosaka et al.

(10) Patent No.: US 9,689,729 B2
(45) Date of Patent: Jun. 27, 2017

(54) ZERO POINT DRIFT COMPENSATING FLOWMETER

(71) Applicant: National Institute of Advanced Industrial Science and Technology, Tokyo (JP)

(72) Inventors: Ryo Kosaka, Tsukuba (JP); Kyouhei Fukuda, Tsukuba (JP); Takashi Yamane, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 60 days.

(21) Appl. No.: 14/438,197

(22) PCT Filed: Oct. 9, 2013

(86) PCT No.: PCT/JP2013/077423
§ 371 (c)(1),
(2) Date: Apr. 23, 2015

(87) PCT Pub. No.: WO2014/065116
PCT Pub. Date: May 1, 2014

(65) Prior Publication Data
US 2015/0253170 A1 Sep. 10, 2015

(30) Foreign Application Priority Data

Oct. 24, 2012 (JP) ................................. 2012-234891

(51) Int. Cl.
*G01F 1/80* (2006.01)
*G01F 1/20* (2006.01)
(Continued)

(52) U.S. Cl.
CPC ................ *G01F 1/78* (2013.01); *A61B 5/026* (2013.01); *G01F 1/206* (2013.01); *G01F 1/50* (2013.01);
(Continued)

(58) Field of Classification Search
None
See application file for complete search history.

(56) References Cited

U.S. PATENT DOCUMENTS 3,090,377 A * 5/1963 Salisbury ........... A61B 5/02133
600/490
3,927,565 A * 12/1975 Pavlin ................... G01F 1/8431
73/861.355
(Continued)

FOREIGN PATENT DOCUMENTS

| JP | 03-264821 A | 11/1991 |
| JP | 04-276519 A | 1/1992 |

(Continued)

OTHER PUBLICATIONS

Extended European Search Report in European Patent Application No. 13848317.7, dated Jun. 13, 2016.
(Continued)

*Primary Examiner* — Harshad R Patel
(74) *Attorney, Agent, or Firm* — Venable LLP; Michael A. Sartori; F. Brock Riggs

(57) ABSTRACT

A small and light-weight flowmeter realizes the compensation of a zero point drift. A mass flowmeter includes: a centrifugal force/centripetal force detection strain gauge adhered to a part acted upon by a centrifugal force or a centripetal force of fluid in a pipe line in which the fluid flows and a flow rate zero point drift compensation strain gauge adhered to a position different from that of the centrifugal force/centripetal force detection strain gauge. A (Continued)

pulse wave propagation time between the two points is used to compensate a zero point drift of a flow rate.

6 Claims, 5 Drawing Sheets

(51) Int. Cl.
    *G01F 1/78*     (2006.01)
    *A61B 5/026*     (2006.01)
    *G01F 1/50*     (2006.01)
    *G01F 15/02*     (2006.01)
    *G01L 13/00*     (2006.01)
    *G01F 1/72*     (2006.01)
    *G01F 1/708*     (2006.01)

(52) U.S. Cl.
    CPC ............... *G01F 1/708* (2013.01); *G01F 1/72* (2013.01); *G01F 1/80* (2013.01); *G01F 15/02* (2013.01); *G01L 13/00* (2013.01)

(56) References Cited

U.S. PATENT DOCUMENTS

| | | |
|---|---|---|
| 5,570,694 A | 11/1996 | Rometsch |
| 5,905,208 A | 5/1999 | Ortiz et al. |
| 6,443,983 B1 * | 9/2002 | Nagyszalanczy ..... A61M 1/101 600/17 |
| 7,500,404 B2 * | 3/2009 | Yamane .................. G01F 1/206 73/861.355 |
| 2004/0088123 A1 | 5/2004 | Ji |
| 2005/0261593 A1 | 11/2005 | Zhang et al. |
| 2007/0193371 A1 | 8/2007 | Yamane et al. |
| 2008/0141789 A1 | 6/2008 | Kassubek et al. |

FOREIGN PATENT DOCUMENTS

| | | |
|---|---|---|
| JP | 11-290285 A | 10/1999 |
| JP | 2001-095766 A | 4/2001 |
| JP | 2007-218775 A | 8/2007 |
| JP | 2009-150671 A | 7/2009 |

OTHER PUBLICATIONS

Marcinkevics et al., "Relationship between arterial pressure and pulse wave velocity using photoplethysmography during the post-exercise recovery period," Acta Universitatis Latviensis, vol. 753, Biology, 2009, pp. 59-68, XP055277168, Retrieved from the Internet: URL: http://eeb.lu.lv/EEB/2009/MarcinkevicsA.pdf.

International Search Report for International Application No. PCT/JP2013/077423, dated Nov. 26, 2013.

International Preliminary Report on Patentability for International Application No. PCT/JP2013/077423, dated May 7, 2015.

* cited by examiner

ZERO POINT DRIFT COMPENSATING FLOWMETER

TECHNICAL FIELD

The present invention relates to a mass flowmeter. In particular, it relates to a sass flowmeter that can be applied to a field requiring the flow rate measurement by a small and light-weight flowmeter e.g., a medical flowmeter such as an artificial heart, or a mass flowmeter that can be applied to the flow rate measurement of the fluid or gas flowing in a piping of a petroleum, petrochemistry, or chemical plant for example, cleaning water for a bottle, cleaning liquid for a wafer or a substrate, or medicinal agent for example.

BACKGROUND ART

This applicant has already filed, as a small and light-weight flowmeter, a mass flowmeter using a rigid band pipe (PTL 1) and a mass flowmeter using an elastic bend pipe (PTL 2). Any of these publications has a disclosure regarding the static pressure compensation and temperature compensation, but has no disclosure regarding the zero point drift compensation.

The mass flowmeter of PTL 3 measures a fluid centrifugal force at a bend pipe end, but has no disclosure regarding the zero point drift compensation.

On the other hand, PTL 4 suggests a method of measuring a blood pressure based on a pulse wave propagation velocity. However, it does not perform a flow rate measurement. Further, PTL 4 uses a specific frequency component of an electrocardiogram to calculate a pulse wave propagation time.

CITATION LIST

Patent Literature

PTL 1: Japanese Patent Laid-Open No. 2007-218775
PTL 2: Japanese Patent Laid-Open No. 2009-150671
PTL 3: Japanese Patent Laid-Open No. H04-276519 (1992)
PTL 4: Japanese Patent Laid-Open No. 2001-95766

SUMMARY OF INVENTION

Technical Problem

For example, a self-contained artificial heart used at the outside of a hospital requires the display of a flow rate for the disease stats control. However, there is no small implantable flowmeter. Industrial flowmeters include various types of flowmeters such as an excess flow meter, a resistance flowmeter or a float-type flowmeter. An ultra-lightweight flowmeter based on a simple measurement method has been required. Conventionally, the mass flowmeter using the bend pipe, which has been suggested by the applicant, uses a simple measurement method and thus can provide a small size. However, since this mass flowmeter uses a strain gauge in a pressure measurement sensor, a sudden temperature change, an external force, or a deteriorated sensor element for example causes a zero point drift in a flow rate measurement value, thus causing a possibility of a measurement error.

Solution to Problem

To solve the aforementioned issue, the present invention provides a pressure sensor and a mass flowmeter. The pressure sensor can compensate a zero point drift in pressure detection means for detecting a pressure of the fluid in a pipe line. The mass flowmeter compensates a zero-point drift in measuring a fluid of the mass flowmeter using a bend pipe.

Specifically, the pressure sensor of the present invention includes a pressure detection means that detects the pressure of fluid in a pipe line in which the fluid flows and a zero point drift compensation pressure detection means that is provided at a position different from that of the pressure detection means. Then, the pulse wave propagation time between these two points and the pressure change amount of the pressure detection means are used to compensate the zero point drift of the pressure of the pressure detection means.

Also according to the mass flowmeter of the present invention, at a part acted upon by the centrifugal force or the centripetal force of the fluid in a pipe line in which fluid flows, a centrifugal, force/centripetal force detection strain gauge is adhere and a flow rate zero point drift compensation strain gauge is adhered at a position different from that of the centrifugal force/centripetal force detection strain gauge. The pulse wave propagation time between these two points is used to compensate the zero point drift of the flow rate.

Also according to the present invention, the mass flowmeter is configured so that a part acted upon by the centrifugal force or the centripetal force of the fluid in the pipe line in which the fluid flows is formed as a bend section in a bend pipe formed by bending the pipe line.

Also according to the present invention, the mass flowmeter is configured so that, at a position different from the part acted upon by the centrifugal force or the centripetal force, a static pressure/temperature compensation strain gauge is adhered to thereby perform a static pressure or temperature compensation.

Also according to the present invention, the mass flowmeter is configured so that a flow rate zero point drift compensation strain gauge is substituted with a signal of the time at which the pulsation of the flow rate generation apparatus is generated or a signal of the opening/closing time of a pressure valve and a signal of a strain gauge adhered to the bend pipe so that the pulse wave propagation time between these two points is used to compensate the zero point drift of the flow rate.

Also according to the present invention, the mass flowmeter is configured so that a tube of elastic material forms between a part acted upon by a centrifugal force or a centripetal force and a part for the zero point drift compensation of the flow rate.

Also according to the present invention, the mass flowmeter also can be used as a pressure meter in a pipe line using the pulse wave propagation time.

Also according to the present invention, the mass flowmeter also can be used to measure the pipe line resistance based on a pressure measured using the pulse wave propagation time and a flow rate measured using the bend pipe.

Advantageous Effects of Invention

According to the present invention, the pulse wave propagation time can be used to compensate the zero point drift of the pressure detection means for detecting the pressure of the fluid in the pipe line. Thus, stable pressure measurement can be realized for a long period.

According to the present invention, the pulse wave propagation time is used in a mass flowmeter using a bend pipe. Thus, when compared with a conventional mass flowmeter, the pressure calculated by the strain gauge of a part acted upon by the centrifugal force or the centripetal force of the fluid and the zero point drift of the pressure calculated by the static pressure/temperature compensation strain gauge can be compensated. Thus, stable flow rate measurement can be realized for a long period even when a sudden temperature change or an external force for example is caused.

Furthermore, since the pulse wave propagation time is not influenced by the viscosity of operating fluid, the mass flow rate can be measured. Furthermore, by the adhesion of the static pressure/temperature compensation strain gauge, a change of the pips line resistance can be coped.

In the conventional case, based on the strain amount of the strain gauge, pressure measurement having a possibility of zero point drift could be carried out. In contrast with this, the present invention provides she pressure measurement for which the zero point drift is compensated. Furthermore, the pipe line resistance can be measured for a long period based on the flow rate and the pressure.

DESCRIPTION OF EMBODIMENTS

Figure 1:
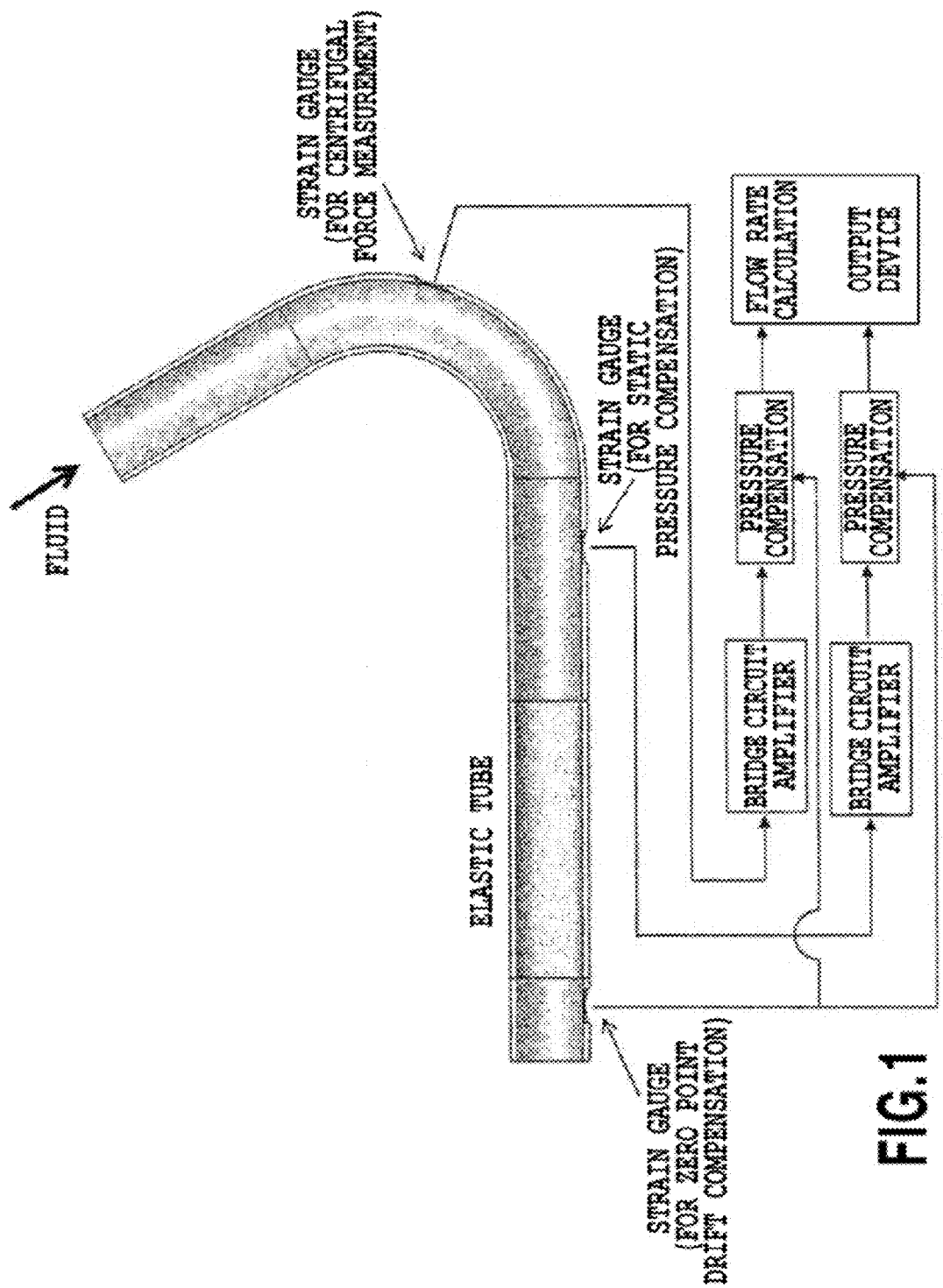
FIG. 1 illustrates a mass flowmeter in which a static pressure or a temperature compensation strain gauge and a zero-point drift compensation strain gauge are added into a mass flowmeter using a bend pipe according to one example of the mass flowmeter of the present invention (first embodiment)

The velocity of a pressure pulse wave moving through a pipe line is called a pulse wave propagation velocity (PWV: Pulse Wave Velocity). When a pulse wave between two different points is recorded in a pipe line, the PWV is defined by the following equation, based on the pulse wave propagation time (PTT: Pulse Transit Time) representing the time difference between the two points and the distance therebetween ($\Delta L$).

$$PWV = \Delta L / PTT$$

On the other hand, the relation between the PWV and the elasticity of the pipe line is expressed by the following equation based on the Moens-Korteweg equation.

$$PWV = \{(E \times h)/(2r \times \rho)\}^{1/2}$$

Here, E is a Young's modulus, h is the thickness of a pipe line wall, r is a radius in the pips line, and $\rho$ is the density of the operating fluid. It is assumed that values other than the Young's modulus are a fixed value because these values have a smaller change amount than that of the Young's modulus. Thus, it is assumed that PWV substantially depends on the Young's modulus. In addition, the Young's modulus can be expressed by the following equation.

$$E = \Delta P/(h \times \Delta D)$$

Here, $\Delta P$ is the pressure change amount, whereas $\Delta D$ is the change amount of the inner diameter, When a constant is set as $\alpha$ and these equations are redefined, the following equation is obtained.

$$PTT = \alpha (\Delta D / \Delta P)^{1/2}$$

As can be seen from this equation, the PTT changes depending on the pressure change amount and the inner diameter change amount. Then, the pressure change amount $\Delta P$ is obtained by a strain gauge adhered to a pipe line. On the other hand, the inner diameter change amount $\Delta D$ of the pipe line at the pressure change amount $\Delta P$ has a lower change amount in accordance with an increase of the minimum pressure value $P_L$. Thus, the following equation is obtained based on the assumption in which the constant is set as $\beta$.

$$\Delta D = \beta \times P_L$$

When the constant is set as $\gamma$ and this equation and the PTT equation are redefined, the following equation is obtained, $$P_L = \gamma \times PTT^2 \times \Delta P$$

That is, it can be seen that the minimum pressure value $P_L$ is a function of the PTT and the pressure change amount $\Delta P$. Furthermore, since the PTT and the pressure change amount $\Delta P$ are not influenced by the zero-point drift, by calculating the constant $\gamma$ in advance from the above equation, the pressure change amount $\Delta P$ is obtained by the strain gauge adhered to the pipe line as described above. Thus, the minimum pressure value $P_L$ can be calculated from the PTT and the above equation. Then, by substituting the value $P_L'$ of the minimum pressure value obtained from the strain gauge adhered to the pipe line with the minimum pressure value $P_L$ obtained from the PTT, the zero point drift of the pressure can be compensated. Then, by calculating the mass flow rate based on the compensated pressure, the zero point drift of the flow rate can be compensated.

[Embodiment]

(First Embodiment)

FIG. 1 illustrates the first embodiment according to one example of the present invention. In a mass flowmeter using three types of strain gauges, a centrifugal force measurement strain gauge is attached to the outer periphery of the bend section, a static pressure compensation strain gauge is attached to a straight pipe section, and a zero point drift compensation strain gauge is attached to a straight pipe section at a position different from that of the bend pipe. When a pressure pulse wave is applied through an inflow opening, each the pulse wave propagation time between the two points are calculated respectively: one between the centrifugal force measurement strain gauge and the zero-point drift compensation strain gauge, the other between the static pressure compensation strain gauge and the zero-point drift compensation strain gauge. Then, signals measured by the centrifugal force measurement strain gauge and the static pressure compensation strain gauge measurement are amplified by an amplifier to calculate a pressure change amount based on a calibration equation calculated in advance. Based on the pulse wave propagation times and the pressure change amounts calculated for the respective pressure pulse waves, the minimum pressure pulse value can be calculated based on the calibration equation calculated in advance. By substituting this minimum pressure pulse value with the minimum pressure value obtained from the strain gauge attached to the pipe line, the zero point drift of the pressure can be compensated. Then, the compensated pressure difference obtained from the two types of strain gauges having bend pipes can be input to the flow rata output device including the flow rate calibration equation, thereby measuring the mass flow rate.

(Second Embodiment)

Figure 2:
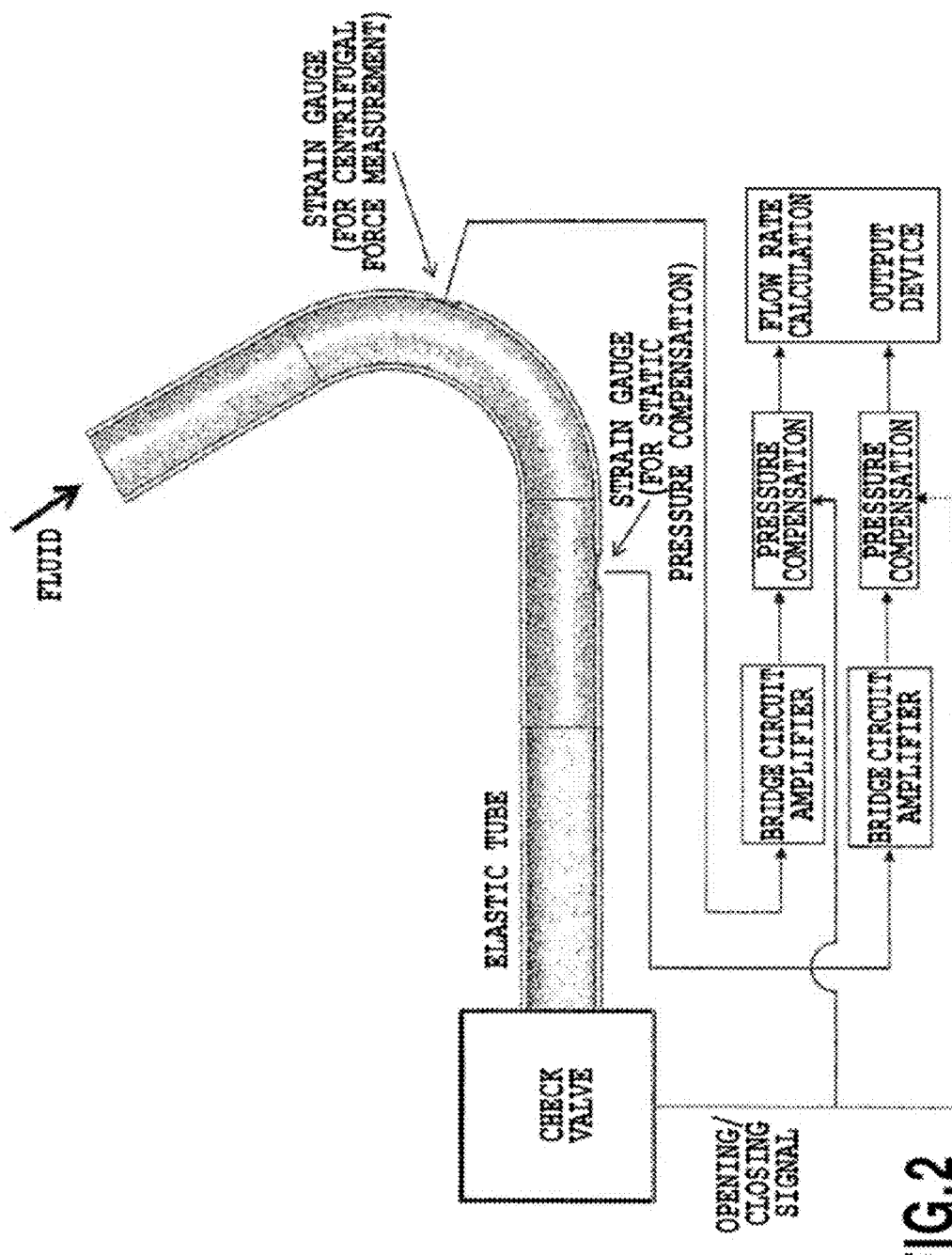
FIG. 2 illustrates a mass flowmeter in which a signal input for the compensation of the zero-point drift from a pressure valve is added into a mass flowmeter using a bend pipe according to one example of the mass flowmeter of the present invention (second embodiment)

FIG. 2 illustrates the second example according to one example of the present invention. In a mass flowmeter using two types of strain gauges, a centrifugal force measurement strain gauge is attached to the outer periphery of the bend section and a static pressure compensation strain gauge is attached to a straight pipe section. A check valve is provided with the downstream of the pipe line. When a fixed pressure is applied to the check valve opens, it opens, and thereby, the fluid flows in the downstream of the pipe line. When a pressure pulse wave is applied through the inflow opening of the pipe line, based on two points of a time at which the check valve opens due to the application of the a fixed pressure and the time at which the two types of strain gauges include therein a fixed pressure change amount, each the pulse wave propagation time between the two points are calculated respectively: one between the two points of the centrifugal force measurement strain gauge and the check valve, the other between the two points of the static pressure compensation strain gauge and the check valve.

Then, the signals measured by she centrifugal force measurement strain gauge and the static pressure compensation strain gauge are amplified by an amplifier to calculate a pressure change amount based on a calibration equation calculated in advance. Based on the pulse wave propagation times and the pressure change amounts calculated for she respective pressure pulse waves, the minimum pressure pulse value can be calculated based on the calibration equation calculated in advance. By substituting this minimum pressure pulse value with the minimum pressure value obtained from the strain gauge attached to the pips line, the zero point drift of the pressure can be compensated. Then, the compensated pressure difference obtained from the two types of strain gauges in bend pipes can be input to the flow rate output device with the flow rate calibration equation, and thereby measuring the mass flow rate.

(Third Embodiment)

Figure 3:
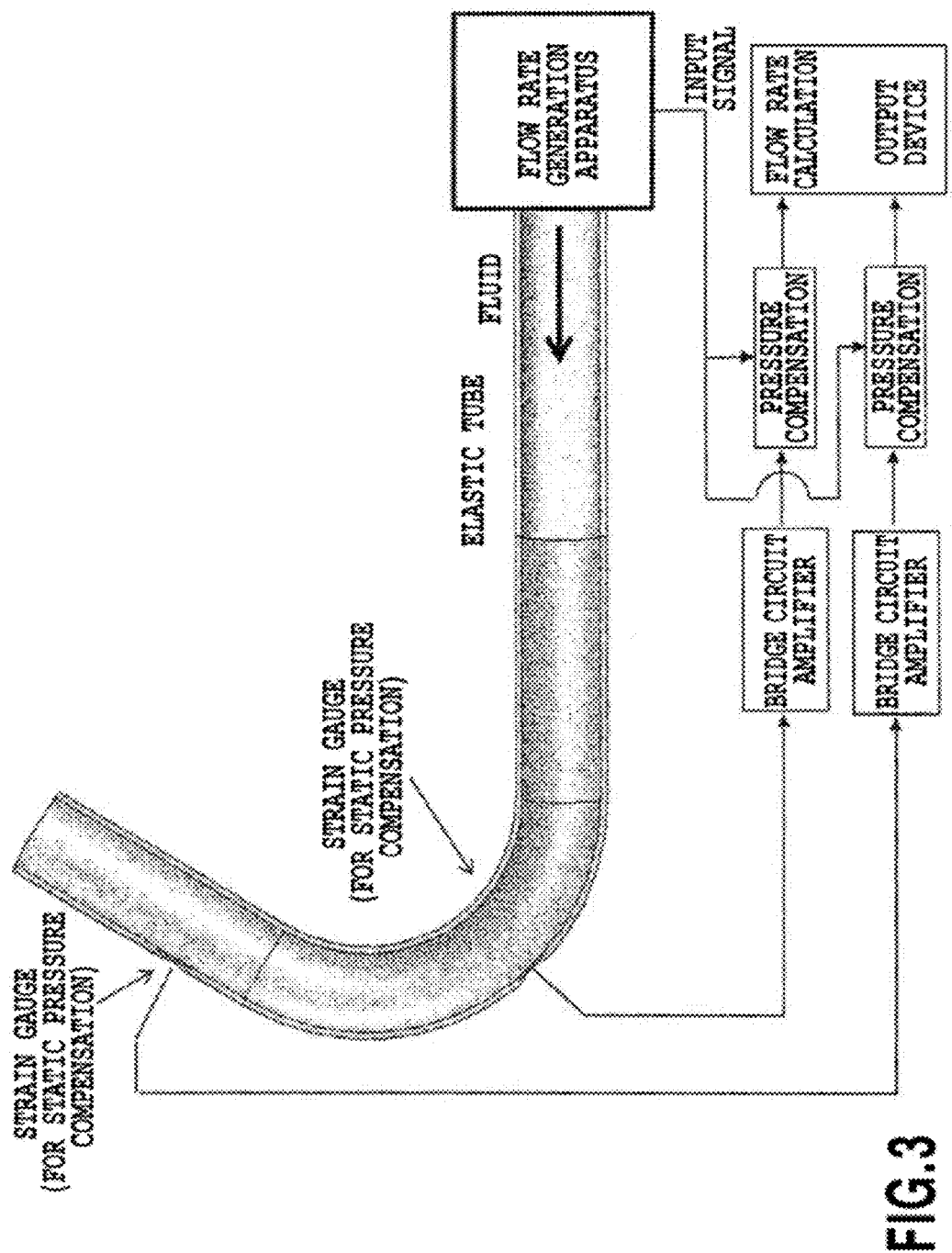
FIG. 3 illustrates a mass flowmeter in which a signal input for the compensation of the zero-point drift from a flow rate generation device is added into a mass flowmeter using a bend pipe according to one example of the mass flowmeter of the present invention (third embodiment)

FIG. 3 illustrates the third example according to one example of the present invention. In a mass flowmeter using two types of strain gauges, a centrifugal force measurement strain gauge is attached to the outer periphery of the bend section and a static pressure compensation strain gauge is attached to a straight pipe section. A flow rate generation device is provided with the upstream of the pipe line. When a pressure pulse wave is applied from the flow rate generation device through the inflow opening of she pipe line, based on two points of a time at which a signal for generating a pressure pulse wave is input so the flow rate generation device and a time at which a fixed pressure change amount occurs in the two types of strain gauges, each the pulse wave propagation time between the two points are calculated respectively: one between the two points of the centrifugal force measurement strain gauge and the flow rate generation device, the other between the two points of the static pressure compensation strain gauge and the flow rate generation device. Then, the signals measured by the centrifugal force measurement strain gauge and the static pressure compensation strain gauge are amplified by an amplifier to calculate a pressure change amount based on a calibration equation calculated in advance. Based on the pulse wave propagation times and the pressure change amounts calculated for the respective pressure pulse waves, the minimum pressure pulse value can be calculated based on the calibration equation calculated in advance. By substituting this minimum pressure pulse value with the minimum pressure value obtained from the strain gauge attached to the pipe line, the zero-point drift of the pressure can be compensated. Then, the compensated pressure difference obtained from the two types of strain gauges in bend pipes can be input to the flow rate output device including the flow rate calibration equation, and thereby measuring the mass flow rate.

Figure 4:
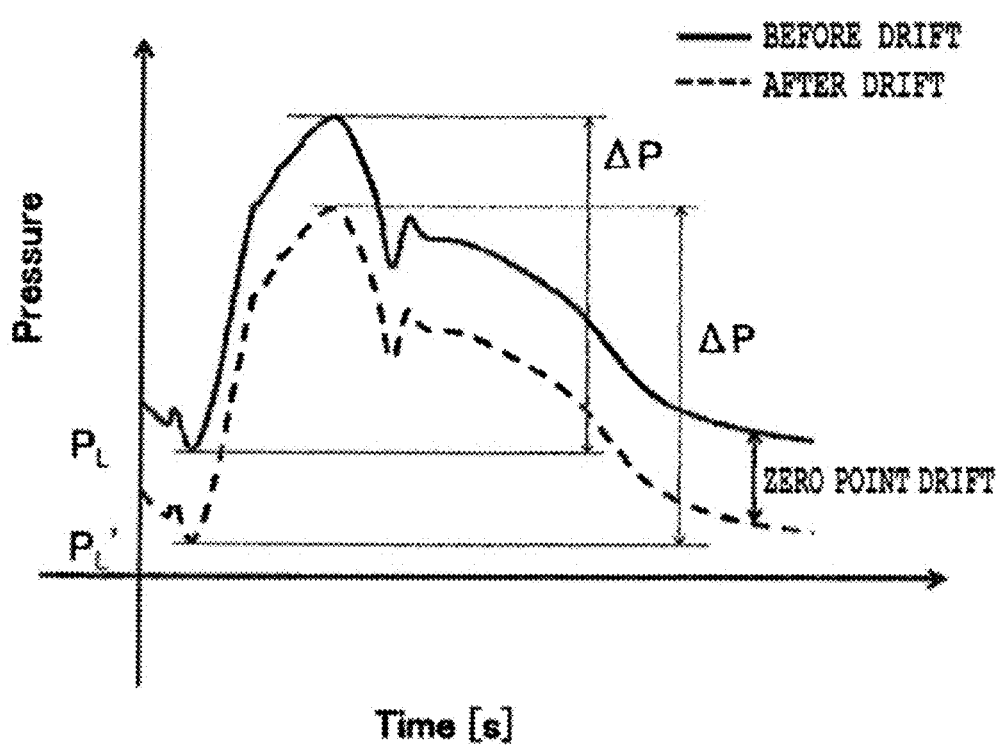
FIG. 4 is a diagram illustrating the zero-point drift (in which the solid line shows an actual pressure waveform and the dotted line shows a pressure waveform during drift)

FIG. 4 is a diagram in which the solid line shows an actual pressure waveform and the dotted line shows a pressure waveform during drift, The vertical axis represents a pressure (pressure), whereas the horizontal axis shows time (time) [s]. In the graph, $P_L$ and $P_{L'}$ are respectively the minimum pressure pulse value before drift and the minimum pressure pulse value after drift. $\Delta P$ is a pressure change amount of the pressure pulse wave. When a strain gauge is used as a sensor for pressure measurement, an external force applied to the pipe line from outside, a temperature change, or a deteriorated sensor element for example causes a zero-point drift in the output of the strain gauge, which undesirably causes the pressure waveform to be drifted from the solid line to the dotted line. Thus, the minimum pressure $P_L$ obtained from the pulse wave propagation velocity and the pressure change amount can be substituted with the minimum pressure $P_{L'}$ after drift, and thereby compensating the zero point drift.

Figure 5:
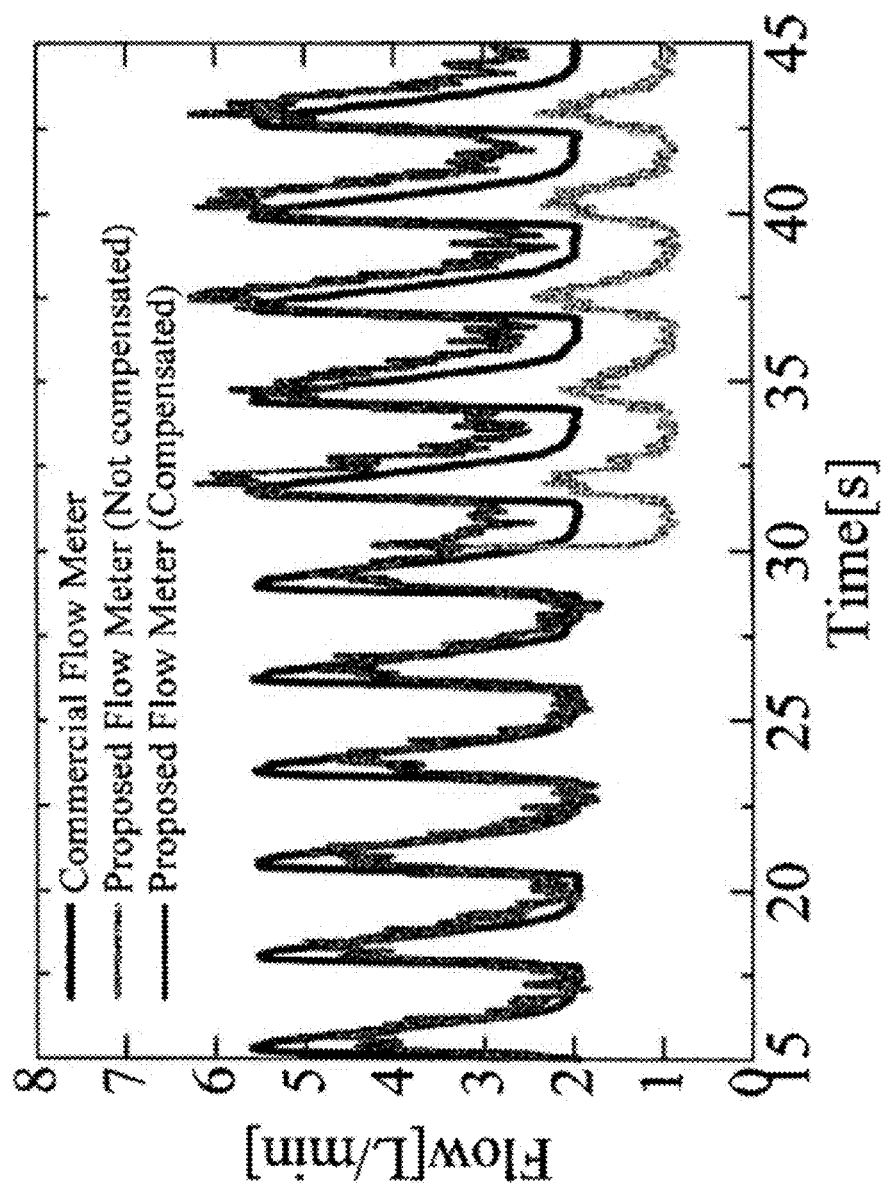
FIG. 5 is a diagram showing experiment results, one without compensating a zero-point drift, and the other with compensating a zero-point drift.

FIG. 5 illustrates one example of the result of an actual measurement test using a round closed circuit. The solid line shows the measurement result of a commercially-available ultrasonic flowmeter. The light gray solid line shows the measurement result of a mass flowmeter for which the zero point drift is not compensated. The dark gray solid line snows the measurement result for which the zero-point drift is compensated. At 30 [s], a zero-point drift was caused in the strain gauge of the mass flowmeter, which resulted in that the mass flowmeter for which the zero-point was not compensated showed a high measurement error when compared to the case of the commercially-available flowmeter. On the other hand, the mass flowmeter for which the zero point was compensated showed a lower measurement error to commercially-available flowmeter when compared with the mass flowmeter for which no zero-point was compensated.

INDUSTRIAL APPLICABILITY

The invention can be applied to a field requiring the flow rate measurement by a small and light-weight flowmeter (e.g., a medical flowmeter such as an artificial heart) or a mass flowmeter that can be applied to the flow rate measurement of the fluid or gas flowing in a piping of a petroleum, petrochemistry, or chemical plant for example, cleaning water for a bottle, cleaning liquid for a wafer or a substrate, or medicinal agent for example, providing the compensation of a zero point drift.

The invention claimed is:
1. A pressure sensor, comprising:
a first pressure detection device configured to detect the pressure of fluid in a pipe line in which the fluid flows; and a second pressure detection device for compensation of a zero point drift configured to detect the pressure of fluid at a position different from a position of the first pressure detection device, wherein the zero point drift of a pressure of the first pressure detection device is compensated by substituting a value of a minimum pressure value obtained from an output of the first pressure detection device with a minimum pressure value obtained from a pulse wave propagation time and a pressure change amount, the pulse wave propagation time representing the time difference propagating between different two portions in the pipe line recorded between the first and second pressure detection devices, the pressure change amount being obtained from the output of the first pressure detection device.

2. A mass flowmeter, comprising:

a first strain gauge disposed in a bent section in a pipe line in which a centrifugal force or a centripetal force of fluid is acted, the fluid flows in the pipe line, and configured to detect the centrifugal force or the centripetal force of fluid; and a second strain gauge which is disposed in the straight section in the pipe line different from the bent section;

a third strain gauge for a static pressure compensation disposed in a straight section in the pipe line different from the second strain gauge, wherein a zero-point drift of a flow rate is compensated by substituting a value of a minimum pressure value obtained from an output of the first strain gauge with a minimum pressure value obtained from a pulse wave propagation time, a second pulse wave propagation time and a pressure change amount, the pulse wave propagation time represents the time difference propagating between different two portions in the pipe line recorded between the first and second strain gauges, the second pulse wave propagation time represents the time difference propagating between the two portions in the pipe line recorded between the second and third strain gauges, and the pressure change amount being obtained from each output of the first and third strain gauges.

3. The mass flowmeter according to claim 2, wherein a tube of elastic material is formed in the different two points in the pipe line between the first and second strain gauges.

4. The mass flowmeter according to claim 2, wherein a signal, after the zero point drift compensation using the pulse wave propagation time, is output as a pressure signal.

5. The mass flowmeter according to claim 4, wherein the pipe line resistance is measured from the pressure signal and the flow rate measured using the bent section.

6. A mass flowmeter, comprising:

a first strain gauge disposed in a bent section in a pipe line in which a centrifugal force or a centripetal force of fluid is acted, the fluid flows in the pipe line, and configured to detect the centrifugal force or the centripetal force of fluid; and a check valve provided in the straight section in the pipe line the check valve configured to open when a fixed pressure is applied to the pipe line, a third strain gauge for a static pressure compensation disposed in a straight section in the pipe line different from the second strain gauge, and wherein a third pulse wave propagation time is calculated based on a time of a fixed pressure change amount in the first strain gauge and an opening time of the check valve, the third pulse wave propagation time represents the time difference propagating between different two portions in the pipe line recorded between the first strain gauge and the check valve, a fourth pulse wave propagation time is calculated based on a time of a fixed pressure change amount in the third strain gauge and an opening time of the check valve, the third pulse wave propagation time represents the time difference propagating between the two portions in the pipe line recorded between the third strain gauge and the check valve, and a zero-point drift of a flow rate is compensated by substituting a minimum pressure value obtained from an output of the first pressure detection device with a minimum pressure value obtained from the third pulse wave propagation time, the fourth pulse wave propagation time and a pressure change amount, the pressure change amount being obtained based on each of the outputs of the first and third strain gauges.

* * * * *